United States Patent [19]

Parry et al.

[11] Patent Number: 4,576,801

[45] Date of Patent: Mar. 18, 1986

[54] PESTICIDAL SHEETS OR CONTAINERS

[75] Inventors: Lawrence J. Parry, Darwin; Bruce J. Morrison, 8 Tasman Circuit, Wagaman, both of Australia

[73] Assignee: Bruce J. Morrison, Australia

[21] Appl. No.: 629,475

[22] PCT Filed: Dec. 20, 1983

[86] PCT No.: PCT/AU83/00188
§ 371 Date: Jul. 13, 1984
§ 102(e) Date: Jul. 13, 1984

[87] PCT Pub. No.: WO84/02447
PCT Pub. Date: Jul. 5, 1984

[30] Foreign Application Priority Data

Dec. 20, 1982 [AU] Australia .............................. PF7337
May 25, 1983 [AU] Australia .............................. PF9526

[51] Int. Cl.⁴ .......................... B05D 5/00; C09D 5/14; A01N 25/34; A61F 13/00
[52] U.S. Cl. ................................... 427/288; 101/426; 106/15.05; 106/20; 424/27; 428/907
[58] Field of Search ................ 424/27; 106/20, 15.05; 427/288; 428/907; 101/426

[56] References Cited

U.S. PATENT DOCUMENTS

| | | | |
|---|---|---|---|
| 1,739,840 | 12/1929 | Kendall | 424/27 X |
| 2,157,449 | 5/1939 | Berg | 424/27 X |
| 3,111,539 | 11/1963 | Bocker et al. | 560/132 |
| 4,102,991 | 7/1978 | Kydonieus | 424/27 |

Primary Examiner—Michael R. Lusignan
Attorney, Agent, or Firm—Larson and Taylor

[57] ABSTRACT

An item (including a sheet or lamina) is treated to proof the item, or a surface or area in which the item is placed, against crawling insects, by printing or spraying the item, or immersing the item in, a pesticide/liquid carrier solution and then drying the solution to remove the liquid carrier, to leave a residue pesticide in or on the material of the item to be contacted by the crawling insects. The pesticide/carrier solution may be applied to the item by mixing the pesticide in a suitable ink and printing the solution onto the item by flexopress, offset or letterpress printing methods or by silk-screening methods.

6 Claims, No Drawings

PESTICIDAL SHEETS OR CONTAINERS

BACKGROUND OF THE INVENTION (1) Field of the Invention

This invention relates to pesticidal sheets, containers or the like and to methods of manufacturing same.

(2) Description of the Prior Art

There are two main methods for applying pesticidal protection to a surface or area. The first method is to apply the pesticide to the surface by mixing it with a liquid carrier, spraying the mixture onto the surface and allowing the liquid carrier to evaporate, leaving the pesticide as a residue. The pests come into contact with the pesticide and die. These pesticides have an effective life of approximately 3 months. However, their effectiveness can be markedly reduced if the surface is washed or becomes damp, removing the pesticide. Because of the nature of spraying the pesticide onto the surface, a uniform distribution of pesticide cannot be assured and so a relative high toxicity level must be used to ensure effectiveness. Even then, areas of the surface may be missed, allowing the pests to pass through a target zone without coming into contact with the pesticide.

The second method is to employ pest strips which contain a vaporizing pesticide which must diffuse throughout the area to be protected. Again, as the pesticide must be effective throughout the whole area, fairly high toxicity levels must be used. As the pesticide must be able to vapourize, it is generally unstable and means must be provided to control the breakdown of the pesticide or the effective life of the strip would only be from a few hours to e.g. 7-10 days.

For example, Australian Pat. No. 491714 (Herculite Protective Fabrics Corporation) discloses a pesticidal strip where a pesticidal impregnated sheet is enclosed in a nonporous container which allows a controlled migration of the pesticide to the surface of the container. The patent states it is essential to use this form of encapsulation as the pesticides are subject to rapid breakdown (or decomposition) at 100° F. and gives examples of pesticides which have effective lives in open atmosphere, of approximately 7-10 days but which may be effective for up to 90 days using the encapsulation method. Should the container be damaged, the pesticides would rapidly lose their effectivness and the user would be exposed to very high toxicity levels with detremental health effects. The pesticides employed rely on their vapourising characteristics, and leave little, if any, residue.

SUMMARY OF THE PRESENT INVENTION

It is an object of the present invention to provide a sheet container or the like, hereinafter referred to as an item, which is provided with the pesticide to protect the item from pest attack and/or to protect at or adjacent a target zone to kill pests which come in contact with the item.

It is a preferred object to provide a pesticidal item where the protection against pests is available at much lower toxicity levels than for conventional methods.

It is a further preferred object to provide a pesticidal item which has a long effective life.

It is a still further preferred object to provide a pesticidal item which can be easily and economically manufactured.

Other preferred objects of the present invention will become apparent from the following description.

In one aspect the present invention resides in a method of manufacturing an item applicable to a surface or area to proof the item, surface or area against crawling insects, the method including the steps of:

(a) mixing a pesticide with a liquid carrier;

(b) applying the pesticide/carrier solution to the item; and (c) drying the solution to remove the liquid carrier and to leave the pesticide in or on the item to be contacted by the crawling insects.

In a second aspect the present invention resides in an item manufactured by the above method.

In one preferred embodiment, the pesticide is applied to the surface(s) of the item by printing the presticide/carrier solution onto the item using e.g. a flexopress, offset press or letterpress. Alternatively, the pesticide may be applied by silk screening methods. In other alternative preferred embodiments, the item is impregnated with the pesticide by immersion of the item in the solution, or by spraying the item with the solution, so that the pesticide is preferably retained in the material of the item as a residue of fine crystals, uniform in size and distributed uniformly throughout the material of the item.

For the printing embodiments, it is preferred that the pesticide is a wettable-powder or liquid pesticide which is soluble in water-based or alcohol based printer's inks or milled inks, or soluble in a suitable common solvent for the pesticide and ink. Preferably the inks are suitable for the flexopress, offset or letterpress methods of printing. A preferred pesticide for this embodiment is sold under the trade mark "WP80" by Bager AG.

For the immersion or spraying embodiments, a preferred pesticide is "Propoxur" (2-Isopropoxy-phenyl-N-methyl) developed by Bager AG and the subject of U.S. Pat. No. 3,111,539 assigned to Bayer. "Propoxur" is also suitable for the printing embodiment. Other commercially available residual contact pesticides may be used for all the embodiments and these include carbamates, such as bendicarb, chlorinated hydrocarbons, organic phosphates such as idophenphos, fenitrochion or Dursban, and pyrethroids, including synthetic pyrethroids.

The pesticide/carrier solution (e.g. pesticide/ink mixture) may be printed or sprayed directly onto the items, or the items immersed in the solution, to proof the items against crawling insect attack or the solution may be applied to sheets, laminae or the like to be placed in a target zone to protect the target zone from the crawling insects. The solution may be applied to e.g. legal or archival documents, or the containers for same, to prevent the insects from destroying the valuable documents.

Suitable sheets or laminae include paper or paperlike materials, paper mache, thin felt, cloth, plastics materials or other suitable liquid absorbent materials. One particularly suitable as the sheets or laminae is newsprint, which is highly absorbent.

Preferably the sheets or laminae can be readily cut to size and shape to enable them to be filled to a surface and the sheets or laminae may be provided with an adhesive backing to enable the sheets or laminae to be fixed to the surface. The sheets or laminae may also be provided with a waterproof membrane to enable the sheets or laminae to break down in soil to leave a pesticidal barrier in the soil.

Preferably the printed items or treated sheets or laminae are odourless and non-staining. Preferably the toxicity level of the pesticidal material in or on the items, sheets or laminae is lower than for conventional methods for using contact pesticides and the toxicity level may be up to e.g. 60% lower, making the items, sheets or laminae safe to handle by humans.

DETAILED DESCRIPTION OF THE PREFERRED EMBODIMENTS

To enable the invention to be fully understood, a number of preferred embodiments will now be described.

EXAMPLE I

Wettable residual pesticide powder sold under the trade mark "WP80" (80% strength) sold by Bayer AG is mixed in water-based printer's ink in the ratio of approximately 30%: 70% by weight. The resultant solution is printed onto a sheet by conventional offset printing methods and the solution dries to leave pesticidal bearing ink on the sheet, the pesticide being in the form of fine crystals substantially uniformly distributed through the ink. (For offset and letterpress printing, the solution may contain up to approximately 30% pesticide, high concentration being usable for flexopress printing). Depending on the thickness and material of the sheet, it may be bound e.g. to a book, typed or printed on as a legal document or formed into a container e.g. a cardboard box. Alternatively, the sheet may be cut to size and shape and placed under a kitchen sink, bathroom vanity unit and/or laundry tub unit.

Tests have shown that if a cockroach is exposed to the pesticide for 2 minutes, it is incapacitated in 45 minutes and dead in less than an hour. The effective life of the pesticide, particularly when used in the printing of a book, may be many years. In this way, the invention may be used to provide protection for legal and archival material at very low cost. The documents may themselves be printed with the ink pesticidal solution or contained in boxes or cartons so printed or in containers supplied with replaceable pesticidal sheets.

EXAMPLE II

A length of pliable paper sheet is drawn from a roll and immersed in a bath containing "Propoxur" dissolved in water at the ratio of 60 ml. to 10 L. The wetted sheet is withdrawn and passed through squeeze rollers to remove the excess liquid. The sheet is then dried using heated air. The resultant sheet has fine crystals of the Propoxur uniformly distributed throughout it. Again, the sheet may be cut to size and shape and placed under a kitchen sink, bathroom vanity unit and laundry tub unit.

After approximately 10 days, all the cockroaches in the house are dead. As the protection remains for 12-18 months, any new cockroaches entering the house are also killed during that period.

As cockroaches forage at night, the effectiveness of the sheets may be further increased by using paper sheet having a "furry" surface which increases the effective surface area of the sheet which the cockroaches can come into contact with.

The sheet may be semi-rigid and supplied in the form of mats or pads, depending on the intended application. The mats or pads may be applied to the floors of ships holds or may be provided as a lining for shipping containers, suitable adhesives being applied to one side of the mat or pad to hold them in place. The sheets may also be placed in pet's kennels to kill fleas or ticks.

To protect young trees, when planting, against termites, the holes for the trees may be lined with paper mache impregnated or printed with pesticide. The tree is planted and the hole is filled in. The paper mache breaks down leaving the pesticide as a residual barrier around the roots of the tree.

To provide a termite barrier for house foundations, a waterproof membrane backing (similar to "Ferticon") is applied to the impregnated or printed "paper" sheet. The sheet breaks down, leaving an even distributed pesticide residue under the concrete slab or around the concrete piles.

As the pesticidal sheets are odourless, non-staining and have a very low toxicity level, they can be easily handled by humans and for domestic applications the sheets can be cut from a roll or mat as required. The sheets are contact killers which are highly effective and can be easily removed, replaced and stored, with an estimated undefinited shelf and an effective life of e.g. 12-18 months.

As can be readily seen the sheets are safe to humans and pets, yet deadly for pests, a claim which few if any currently available pesticides or pest strips can make.

It will be readily apparent to the skilled addressee that the choice of sheets or lamina, pesticidal materials and potential applications is almost unlimited and so various changes and modifications may be made to the embodiments described without departing from the scope of the present invention defined in the appended claims.

We claim:

1. A method of manufacturing an item applicable to a surface or area to proof the item, surface or area against crawling insects, the method including the steps of:
   (a) mixing a pesticide with a liquid carrier, said liquid carrier comprising a printer's ink or ink/solvent mixture and said pesticide comprising a wettable-powder or liquid pesticide soluble in a water-or alcohol-based printer's ink or the solvent;
   (b) applying the pesticide/carrier solution to the surface or surfaces of said item by printing or silk-screening methods; and
   (c) drying the solution to remove the liquid carrier and to leave the pesticide in or on the item to be contacted by the crawling insects.

2. A method as claimed in claim 1 wherein:
a flexopress, offset press or letterpress is used to apply the pesticide/carrier solution to the item.

3. A method as claimed in claim 1 wherein:
the toxicity level of the pesticide is up to 60% lower than the contact pesticides applied by conventional methods and the pesticide is odourless and non-staining.

4. A method as claimed in claim 1 wherein:
the item is a sheet or lamina of paper, newsprint or paper-like materials.

5. A method as claimed in claim 1 or 2 wherein:
the pesticide is a residual contact pesticide retained in or on the material of the item as a residue of fine crystals.

6. A method as claimed in claim 5 wherein:
the pesticide is a contact pesticide including one or more of the following:
"WP80" by Bayer AG; carbamates including "Propoxur" and bendicarb; chlorinated hydrocarbons; organic phosphates including idophenphos, fenitrochion and Dursban; and pyrethroids including synthetic pyrethroids.

* * * * *

UNITED STATES PATENT AND TRADEMARK OFFICE
CERTIFICATE OF CORRECTION

PATENT NO. : 4,576,801
DATED : March 18, 1986
INVENTOR(S) : PARRY et al

It is certified that error appears in the above-identified patent and that said Letters Patent is hereby corrected as shown below:

Column 2, line 16, change "presticide" to --pesticide--.

Column 2, lines 34 and 37, correct spelling of "Bager" to --Bayer--.

Signed and Sealed this

Twenty-fourth Day of February, 1987

Attest:

DONALD J. QUIGG

Attesting Officer            Commissioner of Patents and Trademarks